United States Patent [19]

Linn et al.

[11] Patent Number: 4,587,247

[45] Date of Patent: May 6, 1986

[54] SUBSTITUTED AND UNSUBSTITUTED 13-(ALKOXY)METHOXY DERIVATIVES OF THE AVERMECTIN AGLYCONES, COMPOSITIONS AND USE

[75] Inventors: Bruce O. Linn, Bridgewater; Helmut H. Mrozik, Matawan, both of N.J.

[73] Assignee: Merck & Co., Inc., Rahway, N.J.

[21] Appl. No.: 705,254

[22] Filed: Feb. 25, 1985

[51] Int. Cl.$^4$ .............. A61K 31/365; A61K 31/535; C07D 493/22

[52] U.S. Cl. .................. 514/222; 514/236; 514/252; 514/409; 514/450; 544/6; 544/69; 544/70; 544/229; 544/230; 548/406; 548/407; 549/214; 549/264; 260/330.9

[58] Field of Search .............. 544/6, 69, 70, 229, 544/230; 548/406, 407; 549/214, 264; 514/222, 236, 252, 409, 450; 260/330.9

[56] References Cited

U.S. PATENT DOCUMENTS

| | | |
|---|---|---|
| 3,950,360 | 4/1976 | Aoki et al. .................. 260/343.2 R |
| 4,134,973 | 1/1979 | Fisher et al. .............................. 536/9 |
| 4,171,314 | 10/1979 | Chabala et al. ................. 260/343.41 |
| 4,173,571 | 11/1979 | Chabala et al. ................. 260/343.41 |
| 4,199,569 | 4/1980 | Chabala et al. .................... 536/17 A |
| 4,200,581 | 4/1980 | Fisher et al. ....................... 536/17 A |
| 4,201,861 | 5/1980 | Mrozik et al. ..................... 536/17 A |
| 4,206,205 | 6/1980 | Mrozik et al. ........................... 536/9 |
| 4,310,519 | 1/1982 | Albers-Schonberg et al. ... 536/17 R |

Primary Examiner—Robert W. Ramsuer
Attorney, Agent, or Firm—David L. Rose; Manfred Polk; Michael C. Sudol, Jr.

[57] ABSTRACT

Novel substituted and unsubstituted 13-(alkoxy)methoxy derivatives of the avermectin aglycones are useful as anthelmintic and antiparasitic agents. The compounds are also useful as pesticides and insecticides against agricultural pests. Included herein are novel intermediates useful in the process for preparing said avermectin aglycone derivatives. Compositions of said derivatives and methods of administering said compositions are also disclosed.

12 Claims, No Drawings

SUBSTITUTED AND UNSUBSTITUTED 13-(ALKOXY)METHOXY DERIVATIVES OF THE AVERMECTIN AGLYCONES, COMPOSITIONS AND USE

BACKGROUND OF THE INVENTION

The invention relates to novel substituted and unsubstituted 13-(alkoxy)methoxy avermectin aglycone derivatives useful as antiparasitic agents and to the novel intermediates useful in the process for preparing said derivatives. This invention also relates to compositions of said derivatives and methods of administering said compositions.

The term avermectin (previously referred to as C-076) is used to describe a series of compounds isolated from the fermentation broth of an avermectin producing strain of Streptomyces avermitilis and derivatives thereof. The morphological characteristics of the culture are completely described in U.S. Pat. No. 4,310,519 and are incorporated herein by reference. The avermectin compounds are a series of macrolides, each of which is substituted thereon at the 13-position with a 4'-(α-L-oleandrosyl)-α-L-oleandrose group. Avermectin compounds and the derivatives thereof of this invention have a very high degree of anthelmintic and antiparasitic activity.

DESCRIPTION OF THE PRIOR ART

The avermectin series of compounds from which the derivatives of the invention are derived have the following structure:

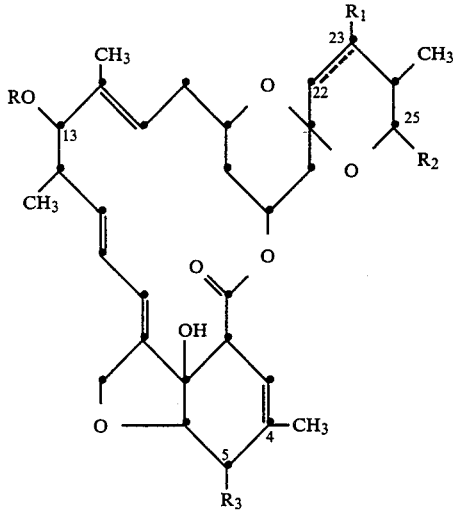

wherein R is the 4'-(α-1-oleandrosyl)-α-1-oleandrose group of the structure:

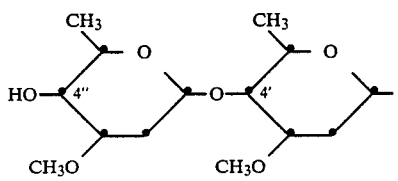

and wherein the broken line indicates a single or a double bond; $R_1$ is hydroxy and is present only when said broken line indicates a single bond;

$R_2$ is iso-propyl or sec-butyl; and
$R_3$ is methoxy or hydroxy.

There are eight different major avermectin natural product compounds and they are given the designations A1a, A1b, A2a, A2b, B1a, B1b, B2a and B2b based upon the structure of the individual compounds.

In the foregoing structural formula, the individual avermectin compounds are as set forth below. (The R group is 4'-(α-L-oleandrosyl)-α-L-oleandrose):

|     | $R_1$       | $R_2$      | $R_3$   |
|-----|-------------|------------|---------|
| A1a | Double Bond | sec-butyl  | —OCH$_3$ |
| A1b | Double Bond | iso-propyl | —OCH$_3$ |
| A2a | —OH         | sec-butyl  | —OCH$_3$ |
| A2b | —OH         | iso-propyl | —OCH$_3$ |
| B1a | Double Bond | sec-butyl  | —OH     |
| B1b | Double Bond | iso-propyl | —OH     |
| B2a | —OH         | sec-butyl  | —OH     |
| B2b | —OH         | iso-propyl | —OH     |

The avermectin compounds are generally isolated as mixtures of homologous a and b components. Such compounds differ only in the nature of the $R_2$ substituent and the minor structural difference has been found to have very little effect on the isolation procedures, chemical reactivity and biological activity of such compounds.

In the isolation of the avermectin compounds from the fermentation broth, which serve as starting materials for the instant processes, the various avermectin compounds will be found to have been prepared in unequal amounts. In particular an "a" series compound will be prepared in a higher proportion than the corresponding "b" series compound. The difference between the "a" series and "b" series is constant throughout the avermectin compounds and consists of a sec-butyl group and an iso-propyl group respectively at the 25-position. This difference, of course, does not interfere with any of the instant reactions. In particular it may not be necessary to separate the "b" components from the related "a" component. Separation of these closely related compounds is often not practiced since the "b" compound often is present only in a small amount, and the structural difference has negligible effect on the reaction processes and biological activities.

In particular it has been found that the starting materials for the compounds of this invention are conveniently prepared in a ratio of about 80% to 95% avermectin B1a or A1a and less than 20% avermectin B1b or A1b. Thus the preferred composition of this invention is one which contains not less than 80% of the "a" component and not more than 20% of the "b" component.

Milbemycin compounds are similar to the above avermectin compounds in that the 16-membered macrocyclic ring is present. However, such compounds have no substitution at the 13-position and have a methyl or ethyl group at the 25-position (the position the $R_2$ group is found in the above structure). To the extent that such milbemycin compounds can be converted to the 13-substituted and unsubstituted (alkoxy)methoxy derivatives, they are to be construed as being within the ambit of this invention. Such milbemycin compounds and the fermentation conditions used to prepared them are described in U.S. Pat. No. 3,950,360. In addition, 13-deoxy-avermectin aglycones are prepared synthetically from the avermectin natural products and are disclosed in U.S. Pat. Nos. 4,171,134 and 4,173,571. Such compounds are very similar to the milbemycins differing from some of the milbemycins in having an isopropyl or sec-butyl rather than a methyl or ethyl group at the 25-position.

SUMMARY OF THE INVENTION

The invention relates to novel substituted and unsubstituted 13-(alkoxy)methoxy derivatives of the avermectin aglycones and processes for preparing the same. The sugar portion of avermectins is replaced with a substituted or unsubstituted (alkoxy)methoxy group which appears to mimic the avermectin disaccharide. In the case of the milbemycins which do not contain a sugar moiety, the substituted or unsubstituted alkoxymethoxy group is added to the 13-position.

Accordingly, it is an object of the invention to provide novel substituted and unsubstituted 13-(alkoxy)methoxy derivatives of the avermectin aglycones that are useful as antiparasitic agents.

A further object of the invention is to provide processes for preparation of said novel compounds.

Another object of the invention is to provide pharmaceutical compositions for administering said novel compounds.

Still another object of the invention is to provide compounds useful as insecticides and pesticides against agricultural pests.

A still further object of the invention is to provide methods for the treatment of animals suffering from parasitic conditions.

These and other objects and advantages of the present invention will become apparent from the following description.

DESCRIPTION OF THE INVENTION

The compounds of the invention have the following structural formula:

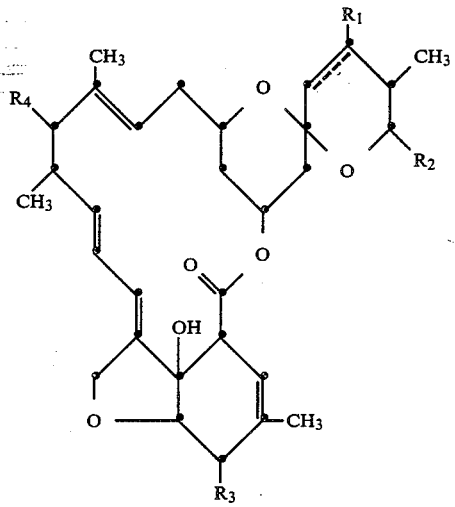

wherein the broken line indicates a single or double bond;

$R_1$ is H, —OH, provided that the broken line indicates a single bond when $R_1$ is OH;

$R_2$ is methyl, ethyl, iso-propyl or sec-butyl;

$R_3$ is OH, $OCH_3$, $OSi(CH_3)_2C(CH_3)_3$;

$R_4$ is X—$(CH_2)_n$—$OCH_2O$— wherein n is an integer ranging from 1 to 6 and X is hydrogen; alkyl $C_{1-6}$ such as methyl, ethyl, isopropyl and the like; alkoxy $C_{1-6}$ such as methoxy, propoxy, iso-butoxy and the like; polyalkoxy, H—$[(CH_2)_pO]_m$— where m and p are integers ranging independently from 1 to 6; such as methoxymethoxy, 2-methoxyethoxy, (2-methoxyethoxy)methoxy, [2-(2-methoxyethoxy)ethoxy]methoxy; and the like; phenyl; phenyl (alkoxy $C_{1-4}$) such as benzyloxy, 2-phenylethoxy and the like; acyloxy $C_{1-4}$ such as formyloxy, acetoxy, propionyloxy and the like; hydroxy; phenyl poly(alkoxy), —$[(CH_2)_pO]_m$— wherein p and m are as defined above such as benzyloxymethoxy, (2-benzyloxyethoxy)methoxy and the like; halogen such as chlorine, bromine and the like; amino; alkylamino $C_{1-5}$ such as methylamino, ethylamino, isobutylamino and the like; dialkylamino $C_{2-8}$ such as dimethylamino, methylethylamino and the like; or heterocyclic 3–6 membered nitrogen containing ring optionally containing an additional oxygen, sulfur or nitrogen heteroatom wherein the ring nitrogen is bonded to the alkoxy group such as aziridino, pyrrolidino, morpholino, thiomorpholino, 4-methylpiperazino and the like.

As will be recognized by those skilled in the art, the foregoing structural formula encompasses several asymmetric centers which will be capable of producing optically active compounds. It is intended that all such optically active isomers, particularly at the 13-position, whether isolated or prepared as racemic mixture or as individual enantiomers are included within the scope of this invention.

Representative examples of the most preferred compounds are:
13-epi-O-benzyloxymethyl-22,23-dihydro avermectin B1a/B1b aglycones,
13-O-(2-chloroethoxy)methyl-22,23-dihydro avermectin B1a/B1b aglycones,
13-O-(2-dimethylaminoethoxy)methyl-22,23-dihydro avermectin B1a/B1b aglycones,
13-[2-(2-methoxyethoxy)ethoxy]methyl-22,23-dihydro avermectin B1a/B1b aglycones,
13-O-(2-methoxyethoxy)methyl avermectin B1a/B1b aglycones,
13-O-(2-methoxyethoxy)methyl-22,23-dihydro avermectin B1a/B1b aglycones,
13-O-(2-methoxyethoxy)methyl avermectin B2a/B2b aglycones,
13-epi-O-(2-methoxyethoxy)methyl-22,23-dihydro avermectin B1a/B1b aglycones,
13-(2-methoxyethoxy)methoxy milbemycin $\alpha_1$,
13-(2-methoxyethoxy)methoxy milbemycin $\alpha_3$,
13-O-[2-(2-methoxyethoxy)methoxyethoxy]methyl-22,23-dihydro avermectin B1a/B1b aglycones,
13-O-methoxymethyl-22,23-dihydro avermectin B1a/B1b aglycones,
13-O-[2-(methoxymethoxy)ethoxy]methyl-22,23-dihydro avermectin B1a/B1b aglycones,
13-[2-(methoxymethoxy)ethoxy]methoxy milbemycin $\alpha_3$,
13-[2-(methoxymethoxy)ethoxy]methoxy milbemycin $\alpha_1$,
13-O-[2-(morpholin-1-yl)ethoxy]methyl-22,23-dihydro avermectin B1a/B1b aglycones.

Other examples of preferred compounds are:
13-O-(2-acetoxyethoxy)methyl-22,23-dihydro avermectin B1a/B1b aglycones,
13-O-(2-methylaminoethoxy)methyl-22,23-dihydro avermectin B1a/B1b aglycones, 13-O-(2-aminoethoxy)methyl-22,23-dihydro avermectin B1a/B1b aglycones.

PREPARATION OF STARTING MATERIALS

The ultimate starting materials for the compounds of this invention are the avermectin and milbemycin fermentation products defined above. Thus it is apparent that additional reactions are required to prepare many of the starting materials for the instant compounds. Specifically, reactions are carried out at the 5, 13, 22, and 23-positions. It is generally preferred to prepare whatever substituents are required at these positions before carrying out the reaction to introduce the 13-position groups, $R_4$, on the substrate. Such a procedure generally avoids undesirable side reactions. This technique is not required, however, and if desired, other sequences may be used. In addition, it is often necessary to protect certain reactive hydroxy groups where reaction with the above reagents is not desired. With the appropriate positions protected, the above reactions may be carried out without affecting the remainder of the molecule. Subsequent to any of the above described reactions the protecting group may be removed and the unprotected product isolated. The protecting group employed is ideally one which may be readily synthesized, will not be affected by the reaction with halomethyl ether reagents and may be readily removed without affecting any other functions of the molecule. It is noted that the instant protected compounds are novel and have considerable anti-parasitic activity. They are included within the ambit of the instant invention. One preferred type of protecting group for the avermectin and milbemycin type of molecule is the tri-substituted silyl group, preferably the trialkyl silyl group. One especially preferred example is the t-butyl dimethylsilyl group. The reaction preparing the protected compound is carried out by reacting the hydroxy compound with the appropriately substituted silylhalide, preferably the silylchloride in an aprotic polar solvent such as dimethylformamide. Imidazole is added as a catalyst. The reaction is complete in from 1 to 24 hours at from 0° to 25° C. For the 5-position hydroxy group the reaction is complete in from ½ to 3 hours at from 0° C. to room temperature. This reaction is selective to the 5 position under the conditions above described and very little, if any, silylation is observed at other hydroxy substituted positions. If it is desired to protect the 23-hydroxy group, a 13, 5,23-tri(phenoxyacetyl) derivative can be prepared. Basic hydrolysis will leave the highly hindered 23-O-substituent but will hydrolyze the 5- and 13-O-phenoxy acetyl groups leaving them available for reaction. The 5-position may be selectively protected as described above with t-butyldimethylsilyl, and the 13-hydroxy group may be reacted.

The silyl group may be removed after the other contemplated reactions may be carried out. The silyl group or groups are removed by stirring the silyl compound in methanol catalyzed by a catalytic amount of an acid, preferably a sulfonic acid such as p-toluenesulfonic acid. The reaction is complete in about 1 to 12 hours at from 0° to 50° C.

Another of the starting materials used in the foregoing reaction scheme are those in which the 22,23 double bond of the A1 and B1 compounds has been reduced to a single bond. As is readily apparent from an analysis of the structure of avermectin starting materials there are 5 unsaturations in the 1-series of compounds. Thus in the "1" series of compounds it is necessary to reduce the 22,23 double bond while not affecting the remaining four unsaturations or any other functional group present on the molecule in order to selectively prepare the 22,23 dihydro avermectins. It is necessary to select a specific catalyst for the hydrogenation, one that will selectively hydrogenate the least hindered from among a series of unsaturations. The preferred catalyst for such a selective hydrogenation procedure is one having the formula:

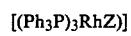

$$[(Ph_3P)_3RhZ]$$

wherein

Ph is phenyl and Z is halogen. The reduction procedure is completely described in U.S. Pat. No. 4,199,569 to Chabala et al.

All of the avermectin starting materials for the compounds of this invention require the removal of both of the α-L-oleandrosyl moieties (described in U.S. Pat. No. 4,206,205 to Mrozik et al.). The selective acylation of the susceptible hydroxy groups is described in U.S. Pat. No. 4,201,861 to Mrozik et al.

The reaction conditions which are generally applicable to the preparation of the aglycone involve dissolving the avermectin compound or the hydrogenated avermectin compound in an aqueous acidic non-nucleophilic organic solvent, miscible with water, preferably dioxane, tetrahydrofuran, dimethoxyethane, dimethylformamide, bis-2-methoxyethyl ether, and the like, in which the water concentration is from 0.1 to 20% by volume. Concentrated acid is added to the aqueous organic solvent to the extent of 1 to 10% by volume. The reaction mixture is generally stirred at about 20°–40° C., preferably at room temperature, for from 6 to 24 hours. The products are isolated, and mixtures are separated by techniques such as column, thin layer, preparative and high pressure liquid chromatography, and other known techniques.

The acids which may be employed in the above process include mineral acids and organic acids such as sulfuric, hydrohalic, phosphoric, trifluoroacetic, trifluoro methane sulfonic and the like. The hydrohalic acids are preferably hydrochloric or hydrobromic. The preferred acid in the above process is sulfuric acid.

A further procedure for the preparation of the aglycone of the avermectin compounds or of the hydrogenated avermectin compounds utilizes a different solvent system. For the preparation of the aglycone, 1% acid, by volume, in methanol under the foregoing reaction conditions has been found to be appropriate.

When this procedure is employed on the starting materials containing the 22,23-double bond, there is a possibility of an acid catalyzed addition of the solvent to the double bond. If such occurs, chromatographic purification will remove the by-product in order to allow for further reactions.

The acids listed above are appropriate for this process, and again sulfuric acid is the preferred acid.

The acylated compounds are prepared using acylation techniques in which the reaction conditions will vary, depending upon the reactivity of the hydroxy group being acylated. Where there is more than one hydroxy group to be acylated, different reaction conditions are employed to minimize the formation of mixtures. The acylation reactions are described completely in U.S. Pat. No. 4,201,861 to Mrozik et al.

The acylation reagents employed are generally the halide, preferably the chloride, of the above loweralkanoyl groups. That is the loweralkanoyl halide reagent is generally employed.

In addition, the acylation reagent could be in the form of the anhydride or of the halo formate. In the case of reactions carried out with the halide reagents, it is often advantageous to include in the reaction mixture a basic compound capable of reacting with and neutralizing the hydrogen halide which is liberated during the course of the reaction. Tertiary amines are preferred such as triethylamine, pyridine, dimethylamino pyridine, diisopropyl ethylamine and the like. The basic compound is required in equimolar amounts relative to the numbered moles of hydrogen halide being liberated, however excess amounts, even using the basic compound as a solvent, are not detrimental. Many other acylation procedures are known in the art and may be used to prepare the above described acylated avermectin and milbemycin compounds.

The A2 compounds have two available hydroxy groups, the 13- and the 23-positions. The 13-position is to be reacted thus the 23-hydroxy group must be protected by selective acylation. This is more readily accomplished by selective hydrolysis of the diacyl compound.

The 13-monoacyl compound will be prepared by using the reaction conditions described above for the A1 compound. Since the 23-hydroxy is less reactive than the 13-position, mild reaction conditions (0° C.) will afford predominantly the 13-monoacyl compound which is the undesired product. Heating the reaction mixture at from room temperature to 100° C. for from 1 to 24 hours will produce the 13, 23-diacyl compound. Since the 23-monoacyl compound is desired, the diacyl compound is treated with aqueous base, such as sodium hydroxide, at room temperature for from 1 to 24 hours. The 13 acyl group will be hydrolyzed leaving the 23 monoacyl compound.

The B1 and 22,23-dihydro B1 compounds have 2 available hydroxy groups: at the 13- and the 5-positions. However, the two hydroxy groups have different reactivities. The 5-hydroxy group can be protected specifically by the preparation of the 5-O-tert-butyldimethylsilyl or other trisubstituted silyl derivative as described by Mrozik et al. in *Tetrahedron Letters* 24 pg 5333–5336 (1983).

The B2 compounds have three hydroxy groups available for substitution: the 13, 5 and 23 positions. In order to prepare the protected starting materials required for the selective reaction of the 13-hydroxy group, the B2 compounds are first converted selectively to the corresponding 5-O-tert-butyldimethylsilyl derivative and then further treated as described above for the A2 compounds containing an unreactive 5-methoxy group.

The necessary starting materials for the preparation of the 13-substituted and unsubstituted alkoxymethoxy milbemycin derivatives, which do not have a 13-hydroxy group, are obtained first by introduction of said hydroxy group into the molecule as described in U.S. Pat. No. 4,134,973. The 13-hydroxy milbemycins are then reacted as described herein for the avermectin aglycones.

DISCUSSION OF CHEMICAL REACTIONS

The instant derivatives are prepared by reacting the appropriately protected avermectin aglycones and milbemycins wherein the 13-position substituent is hydroxy with a halomethyl ether reagent in the presence of a non-reactive acid acceptor such as a sterically hindered tertiary amine in a dry aprotic solvent. The process is outlined in the following general reaction scheme I which for clarity, shows the partial structural formula including only the 10, 11, 12, 13, 14 and 15 ring carbon atoms of the formula:

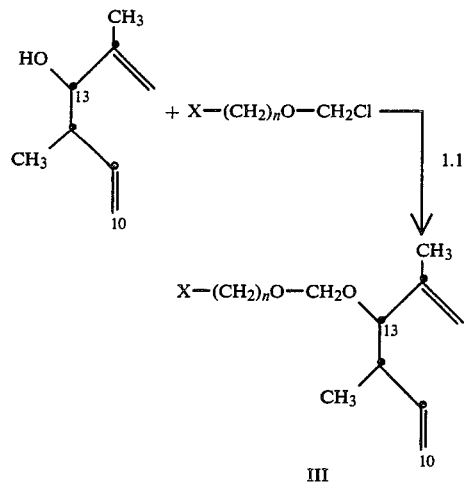

wherein X and n are as previously defined.

The halomethyl ether reagent is used in excess, about eleven equivalents, in order to increase the rate of reaction and to insure a good conversion (1.1). However, it is expected that a lower excess, from 1.1 to 11 equivalents, would also furnish the product. The preferred acid acceptor is N,N-diisopropylethylamine although other hindered non-nucleophilic trialkyl amines are acceptable. Triethyl amine, although reactive with halo methyl ethers, is also satisfactory for this reaction. The amine is used in excess of the halomethyl ether, ranging from 10–18, preferably 13 equivalents of N,N-diisopropylethylamine. The preferred solvent for the most reactive halomethyl ethers is methylene chloride at a concentration of about 4 ml per gram of macrolide. Other aprotic solvents, such as chloroform, tetrahydrofuran and acetonitrile are satisfactory. Temperatures of from 10° to 60° C., preferably from 20° to 40° C. are employed. The reaction is generally complete in from 12 to 24 hours. For less reactive halomethyl ethers, the higher boiling aprotic solvents such as dimethyl formamide and N-methylpyrrolidinone are used so that the reaction temperature can be raised in the range from 25° to 120° C., preferably from 40° to 100° C. The lowest temperature that causes the reaction to proceed at a reasonable rate is employed in order to avoid decomposition (1.1).

A large variety of halomethyl ethers are readily available by the reaction of a selected alcohol such as methanol, isobutanol, 2-methoxy-ethanol, 2-methoxyethoxyethanol, 2-benzyloxyethanol and the like, with paraformaldehyde [$(CH_2O)_{n'}$] in the presence of a hydrogen halide such as HCl, HBr, etc., by a modification of the Henry synthesis as described by H. W. Lucien and C. T. Mason in *J. Am. Chem. Soc.*, 71, 258 (1949) below:

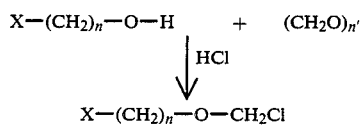

wherein X, n and n' are as previously defined.

Optionally certain 13-substituted(alkoxy)methoxy avermectin aglycones and milbemycins may be prepared by building the 13-position side chain on the macrolide as shown in Scheme II. Reaction of the avermectin aglycones and milbemycins wherein the 13-position is hydroxyl with (2-acetoxyethoxy)methyl bromide prepared according to M. J. Robins and P. W. Hatfield, Can. J. Chem., 60, 547 (1982) furnishes the 13-(2-acetoxyethoxy)methoxy avermectin aglycone and milbemycin derivatives (2.1). The acetyl group is removed with methanolic ammonia providing the corresponding 13-(2-hydroxyethoxy)methoxy (HEM) derivative (2.2) which also serves as a versatile intermediate. Reaction of this intermediate with alkoxy and poly alkoxy chloromethyl ethers furnishes extended poly alkoxy methoxy derivatives of the avermectin aglycones and milbemycins (2.5). The p-nitrobenzenesulfonyloxy (NBS) group is readily displaced providing a variety of 13-substituted ethoxymethoxy derivatives of the avermectin aglycones and milbemycins. The 13-(2-halogenethoxy)methoxy derivatives are obtained upon displacement with halogen ion (2.6). Displacement of the NBS group with ammonia and amines (RRNH where R is selected from hydrogen, alkyl or heterocyclic) furnishes 13-(2-aminoethoxy)methoxy-, 13-(2-alkylaminoethoxy)methoxy-, 13-(2-dialkylaminoethoxy)methoxy-, and 13-(2-heterocyclicaminoethoxy)-methoxy- derivatives of avermectin aglycones and milbemycins (2.7). As the final step, the protected derivatives are deblocked. For example, the 5-O-t-butyldimethylsilyl protecting group is readily removed by reaction with 0.5% to 1.0% p-toluenesulfonic acid monohydrate in methanol.

REACTION SCHEME II

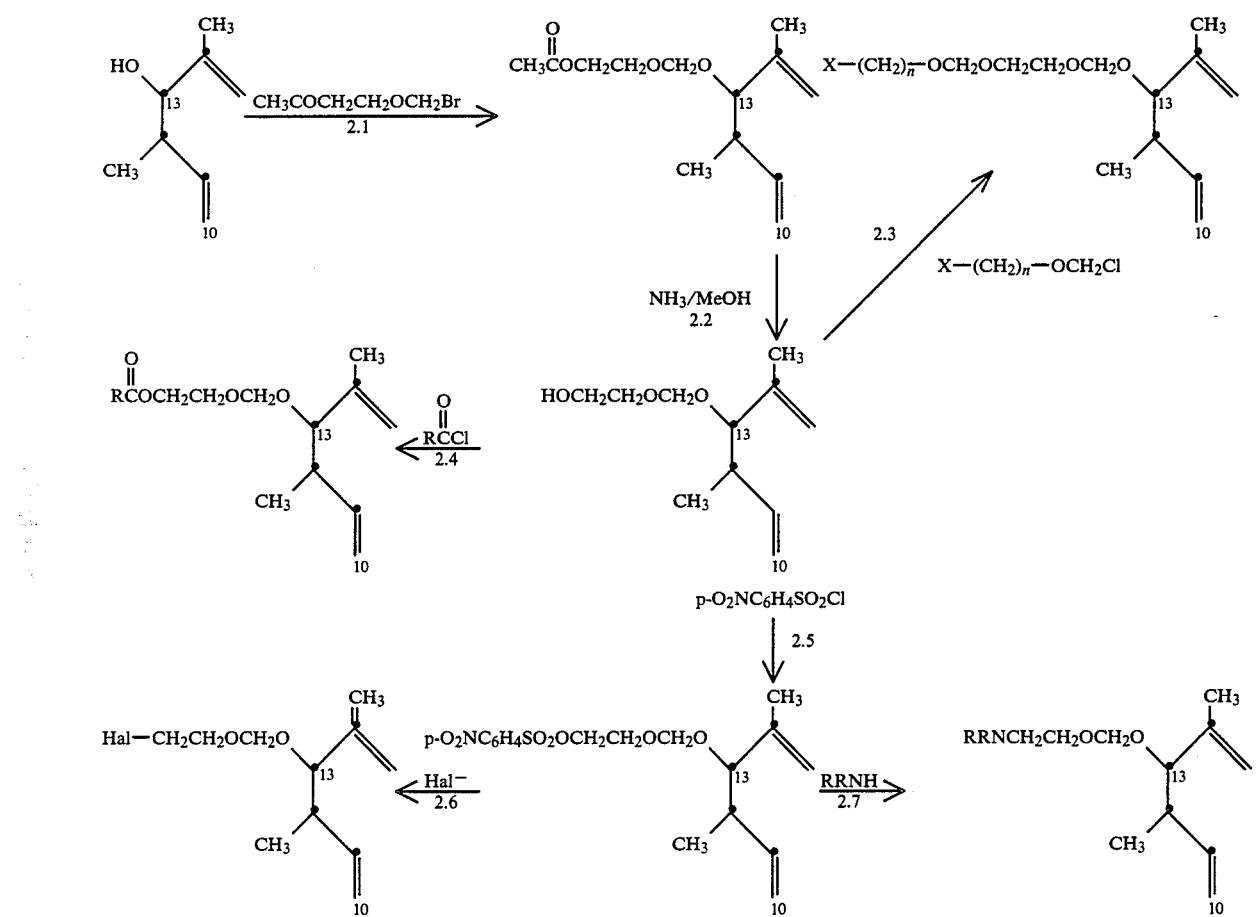

milbemycins (2.3). 13-(2-Acyloxyethoxy)methoxy derivatives of the avermectin aglycones or milbemycins are prepared by treatment of the 13-HEM intermediate with the appropriate acylating agents,

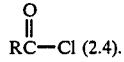

Condensation of the 13-HEM intermediate with p-nitrobenzenesulfonyl chloride provides another useful intermediate, the 13-[2-(p-nitrobenzenesulfonyloxy)ethoxy]methoxy derivative of the avermectin aglycones The 13-epimers of the avermectin aglycones are prepared as outlined in Scheme III below:

REACTION SCHEME III

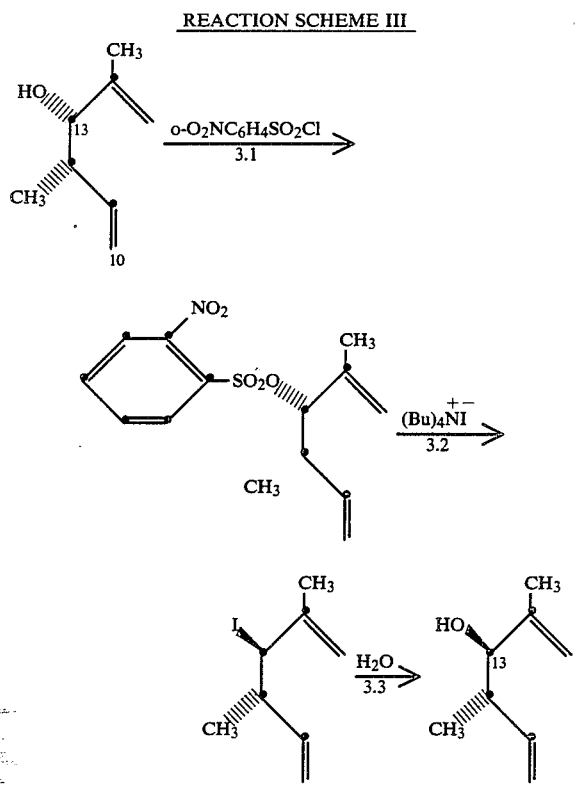

The normal protected avermectin aglycones wherein the 13-position substituent is hydroxy are treated with o-nitrobenzenesulfonyl chloride (3.1) in the presence of a base such as N,N-diisopropylamine, triethylamine and the like and tetrabutylammoniumiodide (3.2) furnishing the 13-epi-iodo-13-deoxy avermectin aglycones and the 13-epi-iodo-milbemycins. The iodo intermediates are heated at 100° C. in 2,6-lutidine and water providing the 13-epi-avermectin aglycones (3.3). These 13-epimers are derivatized by the methods described above furnishing the same types of 13-(alkoxy)methoxy and 13-substituted (alkoxy)methoxy avermectin aglycone derivatives as shown below:

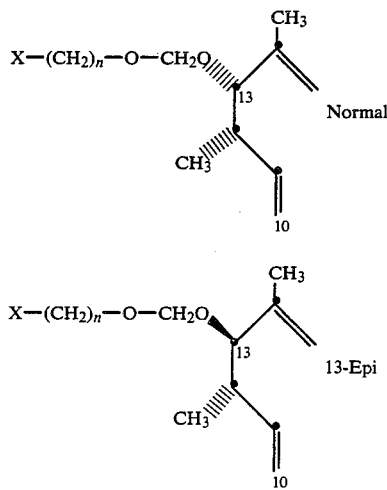

DISCUSSION OF UTILITY

The novel compounds of this invention have significant parasiticidal activity as anthelmintics, ectoparasiticides, insecticides and acaricides, in human and animal health and in agriculture.

The disease or group of diseases described generally as helminthiasis is due to infection of an animal host with parasitic worms known as helminths. Helminthiasis is a prevalent and serious economic problem in domesticated animals such as swine, sheep, horses, cattle, goats, dogs, cats and poultry. Among the helminths, the group of worms described as nematodes causes widespread and often times serious infection in various species of animals. The most common genera of nematodes infecting the animals referred to above are Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris and Parascaris. Certain of these, such as Nematodirus, Cooperia and Oesophagostomum attack primarily the intestinal tract while others, such as Haemonchus and Ostertagia, are more prevalent in the stomach while still others such as Dictyocaulus are found in the lungs. Still other parasites may be located in other tissues and organs of the body such as the heart and blood vessels, subcutaneous and lymphatic tissue and the like. The parasitic infections known as helminthiasis lead to anemia, malnutrition, weakness, weight loss, severe damage to the walls of the intestinal tract and other tissues and organs and, if left untreated, may result in death of the infected host. The substituted avermectin compounds of this invention have unexpectedly high activity against these parasites, and in addition are also active against Dirofilaria in dogs, Namatospiroides, Syphacia, Aspiculuris in rodents, arthropod ectoparasites of animals and birds such as ticks, mites, lice, fleas, blowfly, in sheep Lucilia sp., biting insects and such migrating diperous larvae as Hypoderma sp. cattle, Gastrophilus in horses, and Cuterebra sp. in rodents.

The instant compounds are also useful against parasites which infect humans. The most common genera of parasites of the gastro-intestinal tract of man are Ancylostoma, Necator, Ascaris, Strongyloides, Trichinella, Capillaria, Trichuris, and Enterobius. Other medically important genera of parasites which are found in the blood or other tissues and organs outside the gastrointestinal tract are the filiarial worms such as Wuchereria, Brugia, Onchocerca and Loa, Dracunculus and extra intestinal stages of the intestinal worms Strongyloides and Trichinella. The compounds are also of value against arthropods parasitizing man, biting insects and other dipterous pests causing annoyance to man.

The compounds are also active against household pests such as the cockroach, Blatella sp., clothes moth, Tineola sp., carpet beetle, Attagenus sp., and the housefly *Musca domestica.*

The compounds are also useful against insect pests of stored grains such as Tribolium sp., Tenebrio sp. and of agricultural plants such as 2spider mites, (Tetranychus sp.), aphids, (Acyrthiosiphon sp.); against migratory orthopterans such as locusts and immature stages of insects living on plant tissue. The compounds are useful as a nematocide for the control of soil nematodes and plant parasites such as Meloidogyne spp. which may be of importance in agriculture. The compounds are active against other plant pests such as the southern army worm and Mexican bean beetle larvae.

These compounds may be administered orally in a unit dosage form such as a capsule, bolus or tablet, or as a liquid drench where used as an anthelmintic in mammals. The drench is normally a solution, suspension or dispersion of the active ingredient usually in water together with a suspending agent such as bentonite and a wetting agent or like excipient. Generally, the drenches also contain an antifoaming agent. Drench formulations generally contains from about 0.001 to 0.5% by weight of the active compound. Preferred drench formulations may contain from 0.01 to 0.1% by weight. The capsules and boluses comprise the active ingredient admixed with a carrier vehicle such as starch, talc, magnesium stearate, or di-calcium phosphate.

Where it is desired to administer the avermectin derivatives in a dry, solid unit dosage form, capsules, boluses or tablets containing the desired amount of active compound usually are employed. These dosage forms are prepared by intimately and uniformly mixing the active ingredient with suitable finely divided diluents, fillers, disintegrating agents and/or binders such as starch, lactose, talc, magnesium stearate, vegetable gums and the like. Such unit dosage formulations may be varied widely with respect to their total weight and content of the antiparasitic agent depending upon factors such as the type of host animal to be treated, the severity and type of infection and the weight of the host.

When the active compound is to be administered via an animal feedstuff, it is intimately dispersed in the feed or used as a top dressing or in the form of pellets which may then be added to the finished feed or optionally fed separately. Alternatively, the antiparasitic compounds of our invention may be administered to animals parenterally, for example, by intraruminal, intramuscular, intratracheal, or subcutaneous injection in which event the active ingredient is dissolved or dispersed in a liquid carrier vehicle. For parenteral administration, the active material is suitably admixed with an acceptable vehicle, preferably of the vegetable oil variety such as peanut oil, cotton seed oil and the like. Other parenteral vehicles such as organic preparation using solketal, glycerol formal, and aqueous parenteral formulations are also used. The active avermectin compound or compounds are dissolved or suspended in the parenteral formulation for administration; such formulations generally contain from 0.005 to 5% by weight of the active compound.

Although the antiparasitic agents of this invention find their primary use in the treatment and/or prevention of helminthiasis, they are also useful in the prevention and treatment of diseases caused by other parasites, for example, arthropod parasites such as ticks, lice, fleas, mites and other biting insects in domesticated animals and poultry. They are also effective in treatment of parasitic diseases that occur in other animals including humans. The optimum amount to be employed for best results will, of course, depend upon the particular compound employed, the species of animal to be treated and the type and severity of parasitic infection or infestation. Generally good results are obtained with our novel compounds by the oral administration of from about 0.001 to 10 mg per kg of animal body weight, such total dose being given at one time or in divided doses over a relatively short period of time such as 1-5 days. With the preferred compounds of the invention, excellent control of such parasites is obtained in animals by administering from about 0.025 to 0.5 mg per kg of body weight in a single dose. Repeat treatments are given as required to combat re-infections and are dependent upon the species of parasite and the husbandry techniques being employed. The techniques for administering these materials to animals are known to those skilled in the veterinary field.

When the compounds described herein are administered as a component of the feed of the animals, or dissolved or suspended in the drinking water, compositions are provided in which the active compound or compounds are intimately dispersed in an inert carrier or diluent. By inert carrier is meant one that will not react with the antiparasitic agent and one that may be administered safely to animals. Preferably, a carrier for feed administration is one that is, or may be, an ingredient of the animal ration.

Suitable compositions include feed premixes or supplements in which the active ingredient is present in relatively large amounts and which are suitable for direct feeding to the animal or for addition to the feed either directly or after an intermediate dilution or blending step. Typical carriers or diluents suitable for such compositions include, for example, distillers' dried grains, corn meal, citrus meal, fermentation residues, ground oyster shells, wheat shorts, molasses solubles, corn cob meal, edible bean mill feed, soya grits, crushed limestone and the like. The active hydrogenated avermectin compounds are intimately dispersed throughout the carrier by methods such as grinding, stirring, milling or tumbling. Compositions containing from about 0.005 to 2.0% by weight of the active compound are particularly suitable as feed premixes. Feed supplements, which are fed directly to the animal, contain from about 0.0002 to 0.3% by weight of the active compounds.

Such supplements are added to the animal feed in an amount to give the finished feed the concentration of active compound desired for the treatment and control of parasitic diseases. Although the desired concentration of active compound will vary depending upon the factors previously mentioned as well as upon the particular avermectin derivative employed, the compounds of this invention are usually fed at concentrations of between 0.00001 to 0.002% in the feed in order to achieve the desired antiparasitic result.

The avermectin compounds of this invention are also useful in combatting agricultural pests that inflict damage upon crops while they are growing or while in storage. The compounds are applied using known techniques as sprays, dusts, emulsions and the like, to the growing or stored crops to effect protection from such agricultural pests.

In using the compounds of this invention, the individual substituted avermectin components may be prepared and used in that form. Alternatively, mixtures of two or more of the individual avermectin components may be used, as well as mixtures of the parent avermectin compounds, other avermectin compounds or other active compounds not related to avermectin, with the compounds of this invention.

The following examples are provided in order that this invention might be more fully understood; they are not to be construed as limitative of the invention.

EXAMPLES

The substituted avermectin derivatives prepared in the following examples are generally isolated as amorphous solids and not as crystalline solids. They are thus characterized analytically using techniques such as mass spectrometry, nuclear magnetic resonance, and the like. Being amorphous, the compounds are not characterized by sharp melting points, however, the chromatographic and analytical methods employed indicate that the compounds are pure.

Completion of reaction and purity of products were determined by thin layer chromatography (TLC) and high pressure liquid chromatography (HPLC). TLC was run using Analtech silica gel GF plates and developed with low percentages of methanol in methylene chloride. HPLC was run employing a Whatman Partisil PXS 10/25 ODS-3 reverse phase $C_{18}$ column and solutions containing low percentages of water in methanol with ultraviolet detection at 244 nm.

In the following examples, various starting materials are derivatives of avermectin or milbemycin compounds. The avermectin compounds and the preparation and isolation thereof from fermentation broths are described in U.S. Pat. No. 4,310,519 issued Jan. 12, 1982. The selectively hydrogenated 22,23-dihydro derivatives of avermectin compounds are described in U.S. Pat. No. 4,199,569 issued Apr. 22, 1980. The aglycone derivatives of avermectin compounds are described in U.S. Pat. No. 4,206,205 issued Jan. 3, 1980 and the 13-hydroxy milbemycin derivatives are prepared as described in U.S. Pat. No. 4,134,973 and both are incorporated herein by reference.

EXAMPLE 1

5-O-t-Butyldimethylsilyl-22,23-dihydro avermectin B1a/B1b aglycones t-Butyldimethylsilyl chloride, 4.41 g, was added rapidly to a stirred solution containing 7.64 g of 22,23-dihydro avermectin B1a/B1b aglycones and 4.15 g of imidazole in 23 ml of dry dimethylformamide at room temperature, 22° C. After 3 hours the reaction mixture was poured into 200 ml of water followed by extraction with ether. The ether solution was extracted with water, dried over anhydrous sodium sulfate and evaporated leaving 10.3 g of solid residue. This product was purified by column chromatography using silica gel and methylene chloride furnishing 8.6 g of 5-O-t-butyldimethylsilyl-22,23-dihydro avermectin B1a/B1b aglycones as an amorphous solid. The structure was confirmed by nuclear magnetic resonance, mass spectrometry, ultraviolet and elemental analyses.

EXAMPLE 2

13-O-Methoxymethyl-5-O-t-butyldimethylsilyl-22,23-dihydro avermectin B1a/B1b aglycones Chloromethyl methyl ether 238 μl (3.14 mmol) was added dropwise at ambient temperature (23° C.) to a stirred solution containing 200 mg (285 mmol) of 5-O-t-butyldimethylsilyl-22,23-dihydro avermectin B1a/B1b aglycone and 644 μl (3.71 mmol) of N,N-diisopropylethylamine in 800 μl of dry methylene chloride under nitrogen atmosphere. Stirring was continued until reaction was complete, 20 hours, as determined by TLC. The reaction solution was diluted with methylene chloride, extracted with aqueous sodium bicarbonate and dried over anhydrous sodium sulfate. Evaporation of the methylene chloride solution under reduced pressure gave a crude glass residue product. Purification was accomplished by column chromatography on 5 g of silica gel using methylene chloride-methanol (99:1) followed by preparative TLC on two 1000μ 20×20 cm silica gel plates using methylene chloride-methanol (99.5:0.5) furnishing 90.4 mg of 13-O-methoxymethyl-5-O-t-butyldimethylsilyl-22,23-dihydro avermectin B1a/B1b aglycones as an amorphous solid. Purity was 91% by HPLC. The structure was determined by nuclear magnetic resonance and mass spectrometry.

The above procedure was followed thereby obtaining various 13-O-alkoxymethyl-5-O-t-butyldimethylsilyl-22,23-dihydro avermectin B1a/B1b aglycones by reacting an appropriate α-chloromethyl ether with avermectin aglycones as shown in Table II below:

TABLE II

| Chloromethyl Ether Reactant | 13-Substituent | Identification[2] |
| --- | --- | --- |
| $CH_3OCH_2CH_2OCH_2Cl$ | 13-O—(2-Methoxyethoxy)methyl | A, B, C, E, F |
| $(CH_3)_2CHCH_2OCH_2Cl$ | 13-O—Isobutoxymethyl | A, B, C, E, F |
| $CH_3O(CH_2CH_2O)_2CH_2Cl$[1] | 13-O—[2-(2-Methoxy-ethoxy)ethoxy]methyl | A, B, C, E, F |
| $C_6H_5CH_2OCH_2Cl$[1] | 13-O—Benzyloxymethyl | A, B, C, E, F |

[1]See Example 10
[2]A Magnetic nuclear resonance.
 B Mass spectrometry.
 C Elemental analysis.
 D Ultraviolet analysis.
 E High pressure liquid chromatography.
 F Thin layer chromatography.
 G High resolution mass spectrometry.

EXAMPLE 3

13-O-Methoxymethyl-22,23-dihydro avermectin B1a/B1b aglycones

81 Mg of 13-O-methoxymethyl-5-O-t-butyldimethylsilyl-22,23-dihydro avermectin B1a/B1b aglycones from Example 2 in 5.0 ml of 0.5% para-toluenesulfonic acid monohydrate in methanol was stirred at room temperature (23° C.) until the reaction was complete as determined by TLC. After 50 minutes, the reaction solution was diluted with methylene chloride and extracted with dilute aqueous sodium bicarbonate. The methylene chloride solution was dried over anhydrous sodium sulfate and evaporated under reduced pressure. The residue was chromatographed on two 500μ 20×20 cm silica gel GF plates using methylene chloride-methanol (95:5) furnishing 57.6 mg of 13-O-methoxymethyl-22,23-dihydro avermectin B1a/B1b aglycones as an amorphous solid, purity 90% by HPLC, $E_{1cm}^{1\%}$ 341 at $_{max}^{MeOH}$ 243 nm. The structure was confirmed by nuclear magnetic resonance, mass spectrometry, ultraviolet and elemental analyses.

EXAMPLE 4

5-O-t-Butyldimethylsilyl avermectin B1a/B1b aglycones

Following the procedure of Example 1, 0.67 g of t-butyldimethylsilyl chloride is reacted with 1.17 g of avermectin B1a/B1b aglycones in a solution containing 0.64 g of imidazole in 3.5 ml of dry dimethylformamide. The crude product is purified on silica gel using methylene chloride furnishing the 5-O-t-butyldimethylsilyl avermectin B1a/B1b aglycones.

EXAMPLE 5

13-O-(2-Methoxyethoxy)methyl-5-O-t-butyldimethylsilyl avermectin B1a/B1b aglycones Following the procedure of Example 2, 359 µl of (2-methoxyethoxy)methyl chloride is reacted with 199 mg of the 5-O-t-butyldimethylsilyl avermectin B1a/B1b aglycones from Example 4 in 800 µl of dry methylene chloride containing 644 µl (3.71 mmol) of N,N-diisopropylethylamine. After work up and purification by chromatography on silica gel using methylene chloride-methanol solutions, the 13-O-(2-methoxyethoxy)methyl-5-O-t-butyldimethylsilyl avermectin B1a/B1b aglycones are obtained.

EXAMPLE 6

13-O-(2-Methoxyethoxy)methyl avermectin B1a/B1b aglycones

Following the procedure of Example 3, 80 mg of the 13-O-(2-methoxyethoxy)methyl-5-O-t-butyldimethylsilyl avermectin B1a/B1b aglycones from Example 5 are reacted in 5.0 ml of methanolic 0.5% paratoluenesulfonic acid monohydrate furnishing the 13-O-(2-methoxyethoxy)methyl avermectin B1a/B1b aglycones.

EXAMPLE 7

5,23-Bis-(O-t-Butyldimethylsilyl)avermectin B2a/B2b aglycones t-Butyldimethylsilyl chloride, 292 mg, is added to a stirred solution containing 200 mg of avermectin B2a/B2b aglycones and 266 mg of imidazole in 2.4 ml of dry dimethylformamide at room temperature, 22° C. After 24 hours, the reaction mixture is poured into water and extracted with ether. The ether solution is extracted with water, dried over anhydrous sodium sulfate and evaporated leaving a residue. The residue is chromatographed on silica gel using methylene chloride ethanol solutions furnishing the purified 5,23-bis-(O-t-butyldimethylsilyl)avermectin B2a/B2b aglycones.

EXAMPLE 8

13-O-(2-Methoxyethoxy)methyl-5,23-bis-(O-t-butyldimethylsilyl)avermectin B2a/B2b aglycones Following the procedure of Example 2, 359 µl of (2-methoxyethoxy)methyl chloride is reacted with 237 mg of 5,23-bis-O-t-butyldimethylsilyl avermectin B2a/B2b aglycones from Example 7 in 800 µl of dry methylene chloride containing 644 µl of N,N-diisopropylethylamine. After work up and purification by chromatography on silica gel using methylene chloride methanol solutions the 13-O-(2-methoxyethoxy)methyl5,23-bis-(O-t-butyldimethylsilyl)avermectin B2a/B2b aglycones are obtained.

EXAMPLE 9

13-O-(2-Methoxyethoxy)methyl avermectin B2a/B2b aglycones

13-O-(2-Methoxyethoxy)methyl-5,23-bis-(O-t-butyldimethylsilyl)avermectin B2a/B2b aglycones from Example 8, 30 mg, in 3.0 ml of 1.0% paratoluenesulfonic acid monohydrate in methanol is stirred at room temperature, 22° C., for 2½ hours. The reaction solution is diluted with methylene chloride and extracted with aqueous sodium bicarbonate. The methylene chloride solution is dried over anhydrous sodium sulfate and evaporated. The resulting residue is chromatographed on silica gel plates using methylene chloride ethanol solutions furnishing the 13-O-(2-methoxyethoxy)methyl avermectin B2a/B2b aglycones.

EXAMPLE 10

[2-(2-Methoxyethoxy)ethox]methyl chloride

Hydrogen chloride gas was bubbled into a mixture containing 24 g (200 mmol) of (2-methoxyethoxy)ethanol, 6.0 g (200 mmol) of paraformaldehyde and 22 g (200 mmol) of powdered calcium chloride with stirring and cooling to −5° C. The HCl was continued for 4 hours as the temperature was allowed to rise gradually to 8° C. Celite was added and the reaction filtered. The filtrate was evaporated leaving 29.8 g of a cloudy oil. The oil was dissolved in methylene chloride and dried over molecular sieves. Evaporation furnished 19.3 g of [2-(2-methoxyethoxy)ethoxy]methyl chloride as an oil which was characterized by nuclear magnetic resonance.

EXAMPLE 11

(2-Benzyloxyethoxy)methyl chloride

Following the procedure of Example 3, benzyloxyethanol is reacted with paraformaldehyde and hydrogen chloride gas furnishing (2-benzyloxyethoxy)methyl chloride.

EXAMPLE 12

13-O-(2-Benzyloxyethoxy)methyl-5-O-t-butyldimethylsilyl-22,23-dihydro avermectin B1a/B1b aglycones Following the procedure of Example 2, (2-benzyloxyethoxy)methyl chloride from Example 11 is reacted with 5-O-t-butyldimethylsilyl-22,23-dihydro avermectin B1a/B1b aglycones furnishing after chromatographic purification 13-O-(2-benzyloxyethoxy)methyl-5-O-t-butyldimethylsilyl-22,23-dihydro avermectin B1a/B1b aglycones.

EXAMPLE 13

3-O-(2-Benzyloxyethoxy)methyl-22,23-dihydro avermectin B1a/B1b aglycones

Following the procedure of Example 3, the product from Example 5 is deblocked furnishing 13-O-(2-benzyloxyethoxy)methyl-22,23-dihydro avermectin B1a/B1b aglycones.

EXAMPLE 14

13-Epi-Iodo-13-deoxy-5-O-t-butyldimethylsilyl-22,23-dihydro avermectin B1a/B1b aglycones A solution containing 1.05 g (4.7 mmol) of o-nitrobenzenesulfonyl chloride in 15 ml of methylene chloride was added dropwise over about 30 minutes with stirring to a solution containing 1.00 g (1.43 mmol) of 5-O-t-butyldimethylsilyl-22,23-dihydro avermectin B1a/B1b aglycones, 1.1 ml (6.3 mmol) of N,N-diisopropylethylamine, 770 mg (6.3 mmol) of 4-dimethylaminopyridine and 2.0 g (5.4 mmol) of tetrabutylammonium iodide in 20 ml of methylene chloride at room temperature (23° C.). Stirring was continued for 3.5 hours. The reaction mixture was poured into ice water and diluted with ether. The ether layer was separated and the aqueous layer was extracted with ether. The ether solutions were combined, extracted with water and sodium chloride solutions and dried over magnesium sulfate. Evaporation of the solvent left 1.5 g of residue which was chromatographed on silica gel using methylene chloride. 13-epi-Iodo-13-deoxy-5-O-t-butyldimethylsilyl-22,23-dihydro avermectin B1a/B1b aglycones, 540 mg of yellow foam solid, was obtained. The structure was confirmed by nuclear magnetic resonance and mass spectrometry.

EXAMPLE 15

13-Epi-5-O-t-Butyldimethylsilyl-22,23-dihydro avermectin B1a/B1b aglycones

A solution containing 902 mg of 13-epi-iodo-13-deoxy-5-O-t-butyldimethylsilyl-22,23-dihydro avermectin B1a/B1b aglycones from Example 14 in 5.3 ml 2,6-lutidine and 135 μl of water was sealed under nitrogen and heated at 100° C. for 14.5 hours until no more starting material remained as determined by TLC. The solution was evaporated in vacuo. The residue was dissolved in toluene and evaporated in vacuo. This step was repeated several times in order to remove residual lutidine. The solid residue was extracted with ethyl ether. The insolubles were discarded and the filtrate evaporated in vacuo leaving 1.1 g of solids. These solids were chromatographed on a 2.5 cm ID×17 cm column of silica gel using methylene chloride-methanol (98:2). Two major bands were separated. The slower moving band, 370 mg, was chromatographed on a smaller silica gel column using methylene chloride-methanol (99:1) furnishing 245 mg of 13-epi-5-O-t-butyldimethylsilyl-22,23-dihydro avermectin B1a/B1b aglycones as an amorphous solid, purity 97% by HPLC. The structure was determined by nuclear magnetic resonance and mass spectrometry.

EXAMPLE 16

13-Epi-O-(2-Methoxyethoxy)methyl-5-O-t-butyldimethylsilyl-22,23-dihydro avermectin B1a/B1b aglycones (2-Methoxyethoxy)methyl chloride, 117 μl (946 μmol) was added to a solution containing 60 mg (86 μmol) of 13-epi-5-O-t-butyldimethylsilyl-22,23-dihydro avermectin B1a/B1b aglycones from Example 15 and 195 μl (1.12 mmol) of N,N-diisopropylethylamine in 240 μl of dry methylene chloride under nitrogen. The solution was stirred and warmed at 40° C. for 16 hours. Workup as in Example 2 was followed by purification on two 500μ 20×20 cm silica gel GF plates using methylene chloride-methanol (98.5:1.5). The major band was chromatographed by TLC once again using ethyl ether-petroleum ether (20:80) furnishing 30.5 mg of 13-epi-O-(2-methoxyethoxy)methyl-5-O-t-butyldimethylsilyl avermectin B1a/B1b aglycones, 90% purity by HPLC. The structure was confirmed by nuclear magnetic resonance and mass spectrometry.

EXAMPLE 17

13-Epi-O-Benzyloxymethyl-5-O-t-butyldimethylsilyl-22,23-dihydro avermectin B1a/B1b aglycones Following the procedure of Example 9, utilizing 100 mg (143 μmol) of the 13-epi-hydroxy aglycone from Example 8, 218 μl (1.57 mmol) of benzyloxymethyl chloride, 241 μl (1.86 mmol) of N,N-diisopropylethylamine in 400 μl of dry methylene dichloride for 3 days at room temperature, 23° C., there was obtained 20.9 mg of 13-epi-O-benzyloxymethyl-5-O-t-butyldimethylsilyl-22,23-dihydro avermectin B1a/B1b aglycones as an amorphous solid, 94% purity by HPLC. The structure was confirmed by nuclear magnetic resonance.

EXAMPLE 18

13-O-(2-Acetoxyethoxy)methyl-5-O-t-butyldimethylsilyl-22,23-dihydro avermectin B1a/B1b aglycones (2-Acetoxyethoxy)methyl bromide, 9.0 ml (52 mmol) was added dropwise to a solution containing 2.8 g (4.0 mmol) of 5-O-t-butyldimethylsilyl-22,23-dihydro avermectin B1a/B1b aglycones and 5.5 ml (44 mmol) of N,N-diisopropylethylamine in 11 ml of methylene chloride. The exotherm was controlled by cooling, maintaining the reaction temperature at 30°–40° C. The solution was stirred at 40° C. until complete as determined by HPLC using methanol-water 95:5 at 1.5 ml/minute, 74 atmospheres. After 28 hours of heating, the reaction was diluted with methylene chloride and stirred for about 30 minutes with saturated aqueous sodium bicarbonate. The methylene chloride layer was separated, extracted with aqueous sodium bicarbonate, dried over anhydrous sodium sulfate and evaporated under reduced pressure leaving 3.86 g of a viscous residue. The residue was chromatographed on a column of silica gel, 260 g, using methylene chloridemethanol with increasing concentrations of methanol from 0.2% to 0.6% furnishing 1.57 g of 13-O-(2-acetoxyethoxy)methyl-5-O-t-butyldimethylsilyl-22,23-dihydro avermectin B1a/B1b aglycones as an amorphous solid. The structure was confirmed by nuclear magnetic resonance and mass spectrometry.

EXAMPLE 19

13-O-(2-Hydroxyethoxy)methyl-5-O-t-butyldimethylsilyl-22,23-dihydro avermectin B1a/B1b aglycones 50 Ml of cold (0°–5° C.) saturated methanolic ammonia was added to a flask containing 1.70 g of 13-O-(2-acetoxyethoxy)methyl-5-O-t-butyldimethylsilyl22,23-dihydro avermectin B1a/B1b aglycones obtained from Example 18. The system was sealed and the solution stirred at room temperature (23° C.), until the reaction was nearly complete as determined by HPLC as described above using methanol-water (95:5), 1.5 ml/minute, 74 atmospheres. The reaction must be stopped before epimerization at $C_2H$ occurs. After $3\frac{2}{3}$ hours, the reaction solution was concentrated in vacuo leaving 1.71 g of crude product as a foam solid. This solid was chromatographed on a 300 g column of silica gel using methylene chloride-methanol (99.4:0.6:0.06) as eluant furnishing 1.11 g of 13-O-(2-hydroxyethoxy)methyl-5-O-t-butyldimethylsilyl-22,23-dihydro avermectin B1a/B1b aglycones as an amorphous solid, $E_{1cm}^{1\%}$ 449 at $\lambda_{max}^{MeOH}$ 243 nm, 97% purity by HPLC. The structure was confirmed by nuclear magnetic resonance and mass spectrometry.

EXAMPLE 20

13-O-[2-(Methoxymethoxy)ethoxy]methyl-5-O-t-butyldimethylsilyl-22,23-dihydro avermectin B1a/B1b aglycones Chloromethyl methyl ether, 100 μl (1.32 mmol)], was added dropwise while stirring and ice bath cooling to a solution containing 90 mg (0.12 mmol) of the 13-O-(2-hydroxyethoxy)methyl-5-O-t-butyldimethylsilyl-22,23-dihydro avermectin B1a/B1b aglycones from Example 19 and 271 μl (1.56 mmol) of N,N-diisopropylethylamine in 0.36 ml of dry methylene chloride. The ice bath was removed and stirring continued at room temperature (23° C.), until the 18 hour reaction was complete as determined by HPLC as described above using methanol-water (95:5), 1.5 ml/minute, 76 atmospheres. The reaction solution was diluted with methylene chloride, extracted with aqueous sodium bicarbonate, dried over anhydrous sodium sulfate and evaporated in vacuo leaving 107 mg of a crude product residue. This residue was chromatographed on two 300–1700 $\mu$20×20 cm silica gel GF plates using methylene chloride-ethyl acetate (97:3). The major band was eluted furnishing 65.8 mg of 13-O-[2-(methoxymethoxy)ethoxy]methyl-t-butyldimethylsilyl-22,23-dihydro avermectin B1a/B1b aglycones as an amorphous solid, 87% purity by HPLC, $\lambda_{max}^{MeOH}$ 243 nm, $E_{1cm}^{1\%}$ 389. The structure was confirmed by nuclear magnetic resonance, mass spectrometry and elemental analyses.

Some of the products prepared by this procedure required multiple preparative TLC using alumina GF and/or silica gel GF plates and either methylene chloride-ethyl acetate or methylene chloride-methanol eluants.

The above procedure is followed, thereby obtaining various 13-O-polyalkoxy methyl-5-O-t-butyldimethylsilyl-22,23-dihydro avermectin B1a/B1b aglycones by reacting an appropriate alkoxy chloromethyl ether with 13-O-(2-hydroxyethoxy)methyl avermectin aglycones as shown in Table III below:

TABLE III

| Chloromethyl Ether Reactant | 13-Substituent | Identification[2] |
|---|---|---|
| $CH_3OCH_2CH_2OCH_2Cl$ | 13-O—[2-(2-Methoxyethoxy)methyoxyethoxy]methyl | A, B, C, D, E, F |
| $CH_3O(CH_2CH_2O)_2CH_2Cl$[1] | 13-O—(2-[2-(2-Methoxyethoxy)-ethoxy]methoxyethoxy)methyl | A, B, E, F |
| $C_6H_5CH_2OCH_2Cl$ | 13-O—[2-(Benzyloxymethoxy)ethoxy]-methyl | A, B, C, F |

[1]See Example 10
[2]See footnote 2 of Table II

EXAMPLE 21

13-O-[2-(2-Benzyloxyethoxy)methoxyethoxy]methyl-5-O-t-butyldimethylsilyl-22,23-dihydro avermectin B1a/B1b aglycones Following the procedure of Example 20, (2-benzyloxyethoxy)methylchloride from Example 11 is reacted with 13-O-(2-hydroxyethoxy)methoxy-5-O-t-butyldimethylsilyl-22,23-dihydro avermectin B1a/B1b aglycones from Example 19 furnishing after chromatographic purification 13-O-[2-(2-benzyloxyethoxy)methoxyethoxy]methyl-5-O-t-butyldimethylsilyl-22,23-dihydro avermectin B1a/B1b aglycones.

EXAMPLE 22

13-O-[2-(2-Benzyloxyethoxy)methoxyethoxy]methyl-22,23-dihydro avermectin B1a/B1b aglycones Following the procedure of Example 3 the product of Example 21 is deblocked furnishing 13-O-[2-(2-benzyloxyethoxy)methoxyethoxy]methyl-22,23-dihydro avermectin B1a/B1b aglycones.

EXAMPLE 23

13-O-(2-Propionyloxyethoxy)methyl-5-O-t-butyldimethylsilyl-22,23-dihydro avermectin B1a/B1b aglycones Propionyl chloride, 9.6 $\mu$l (110 $\mu$mol), is added to a solution at room temperature (22° C.), containing 77.5 mg (100 $\mu$mol) of 13-O-(2-hydroxyethoxy)methyl-5-O-t-butyldimethylsilyl avermectin B1a/B1b aglycones from Example 19, 27 mg (220 $\mu$mol) of 4-dimethylaminopyridine and 77 $\mu$l (440 $\mu$mol) of N,N-diisopropylethylamine in 1.0 ml of dry methylene chloride. Stirring at 22° C. is continued until reaction is complete as determined by TLC or HPLC. The reaction mixture is diluted with methylene chloride, extracted with aqueous sodium bicarbonate, with aqueous 5% potassium dihydrogen phosphate once again with aqueous sodium bicarbonate and then dried over anhydrous sodium sulfate. Evaporation of the solvent in vacuo leaves the crude product as a residue. Purification on silica gel using methylene chloride-methanol furnishes 13-O-(2-propionyloxyethoxy)methyl-5-O-t-butyldimethylsilyl-22,23-dihydro avermectin B1a/B1b aglycones as an amorphous solid.

EXAMPLE 24

13-O-(2-Propionyloxyethoxy)methyl-22,23-dihydro avermectin B1a/B1b aglycones

Following the procedure from Example 3, the product from Example 23 is deblocked furnishing 13-O-(2-propionyloxyethoxy)methyl-22,23-dihdyro avermectin B1a/B1b aglycones.

EXAMPLE 25

13-O-(2-Chloroethoxy)methyl-5-O-t-butyldimethylsilyl-22,23-dihydro avermectin B1a/B1b aglycones p-Nitrobenzenesulfonyl chloride, 73 mg (0.33 mmol) was added while stirring to a solution at room temperature (22° C.), containing 62 mg (80 $\mu$mol) of 13-O-(2-hydroxyethoxy)methyl-5-O-t-butyldimethylsilyl avermectin B1a/B1b aglycones from Example 19, 33 $\mu$l (0.34 mmol) of N,N-diisopropylethylamine and 42 mg (0.34 mmol) of 4-dimethylaminopyridine in 1.0 ml of dry dimethylformamide. Stirring at 22° C. was continued for 9 hours. The reaction mixture was diluted with methylene chloride, extracted with aqueous sodium bicarbonate, with aqueous 5% potassium dihydrogen phosphate, again with aqueous sodium bicarbonate, dried over anhydrous sodium bicarbonate. Evaporation of the solvent in vacuo left 62 mg of an orange foam. This crude was purified on two 500$\mu$ 20×20 cm silica gel GF plates using methylene chloride-methanol-water (99.6:0.4:0.04) furnishing 43 mg of 13-O-(2-chloroethoxy)methyl-5-O-t-butyldimethylsilyl-22,23-dihydro avermectin B1a/B1b aglycones as an amorphous solid, 95% purity by HPLC. The structure was confirmed by nuclear magnetic resonance and mass spectrometry.

EXAMPLE 26

13-O-[2-(p-Nitrobenzenesulfonyloxy)ethoxy]methyl-5-O-t-butyldimethylsilyl-22,23-dihydro avermectin B1a/B1b aglycones p-Nitrobenzenesulfonylchloride 127 mg (574 mmol) in 3.5 ml of dry dimethylformamide was added dropwise to an ice bath cooled solution at 0° C. containing 105 mg (135 $\mu$mol) of 13-O-(2-hydroxyethoxy)methyl-5-O-t-butyldimethylsilyl-22,23-dihydro avermectin B1b/B1b aglycones from Example 19, 134 $\mu$l (770 $\mu$mol) of N,N-diisopropylethylamine and 94.1 mg (770 $\mu$mol) of 4-dimethylaminopyridine in 10.5 ml of dry methylene chloride. Stirring was continued at 0° C. for one hour until reaction was complete as determined by HPLC. The cold reaction solution was diluted with methylene chloride, extracted with aqueous sodium bicarbonate, with 5% aqueous potassium dihydrogen phosphate, once again with aqueous sodium bicarbonate and then dried over anhydrous sodium sulfate. Evaporation of the solvent in vacuo left 118 mg of 13-O-[2-(p-nitrobenzenesulfonyloxy)ethoxy]methyl-5-O-t-butyldimethylsilyl-22,23-dihydro avermectin B1a/B1b aglycones as an amorphous orange solid, 75% purity by HPLC. This product was used directly for displacement reactions. Purification on silica gel using methylene chloride-methanol-water (99.6/0.4/0.04) furnished the product with 99% purity (by HPLC). The structure was confirmed by nuclear magnetic resonance and mass spectrometry.

EXAMPLE 27

13-O-(2-Dimethylaminoethoxy)methyl-5-O-t-butyl-dimethylsilyl-22,23-dihydro avermectin B1a/B1b aglycones Excess dimethylamine gas was bubbled into a solution at room temperature (21° C.) containing 114 mg of 13-O-[2-(p-nitrobenzenesulfonyloxy)ethoxy]methyl-5-O-t-butyldimethylsilyl-22,23-dihydro avermectin B1a/B1b aglycones from Example 26 in 30 ml of dry methylene chloride. The solution was stirred at 21° C. until the 3 hours reaction was complete as determined by HPLC and TLC. The reaction solution was evaporated by nitrogen. The residue was taken up in methylene chloride and extracted with aqueous sodium bicarbonate. The solution was dried over anhydrous sodium sulfate and evaporated in vacuo leaving 94.8 mg of crude product residue. The product was purified by column chromatography on silica gel using methylene chloride-methanol furnishing 43 mg of 13-O-(2-dimethylaminoethoxy)methyl-5-O-t-butyldimethylsilyl-22,23-dihydro avermectin B1a/B1b aglycones as an amorphous solid, 93% purity by HPLC. The structure was confirmed by nuclear magnetic resonance and mass spectrometry.

EXAMPLE 28

13-O-(2-Methylaminoethoxy)methyl-5-O-t-butyldimethylsilyl-22,23-dihydro avermectin B1a/B1b aglycones Following the procedure of Example 27 excess methylamine gas is reacted with 114 mg of 13-O-[2-(p-nitrobenzenesulfonyloxy)ethoxy]methyl-5-O-t-butyl-dimethylsilyl-22,23-dihydro avermectin B1a/B1b aglycones in 30 ml of dry methylene chloride. Work up and chromatographic purification affords the 13-O-(2-methylaminoethoxy)methyl-5-O-t-butyldimethylsilyl-22,23-dihydro avermectin B1a/B1b aglycones.

EXAMPLE 29

13-O-(2-Methylaminoethoxy)methyl-22,23-dihydro avermectin B1a/B1b aglycones

Following the procedure of Example 9, 30 mg of the product from Example 28 is treated with 30 ml of 1.0% para-toluenesulfonic acid monohydrate in methanol until reaction is complete followed by chromatographic purification providing 13-O-(2-methylaminoethoxy)-methyl-22,23-dihydro avermectin B1a/B1b aglycones.

EXAMPLE 30

13-O-(2-Aminoethoxy)methyl-5-O-t-butyldimethylsilyl-22,23-dihydro avermectin B1a/B1b aglycones Following the procedure of Example 27, excess ammonia gas is reacted with 114 mg of 13-O-[2-(p-nitrobenzenesulfonyloxy)ethoxy]methyl-5-O-t-butyl-dimethylsilyl-22,23-dihydro avermectin B1a/B1b aglycones in 30 ml of dry ethylene dichloride in a closed system. The temperature is raised until the reaction proceeds. After completion of reaction as determined by TLC and HPLC, the reaction mixture is worked up and chromatographically purified furnishing 13-O-(2-aminoethoxy)methyl-5-O-t-butyldimethylsilyl)-22,23-dihydro avermectin B1a/B1b aglycones.

EXAMPLE 31

13-O-(2-Aminoethoxy)methyl-22,23-dihydro avermectin B1a/B1b aglycones

Following the procedure of Example 9, 30 mg of the product from Example 30 is treated with 3.0 ml of 1.0% para-toluenesulfonic acid monohydrate in methanol followed by chromatographic purification on silica gel using methylene chloride methanol solutions furnishing the 13-O-(2-aminoethoxy)methyl-22,23-dihydro avermectin B1a/B1b aglycones.

EXAMPLE 32

13-O-[2-(Morpholin-1-yl)ethoxy]methyl-5-O-t-butyl-dimethylsilyl-22,23-dihydro avermectin B1a/B1b aglycones Morpholine 500 μl (5.7 mmol) was added with stirring at room temperature (23° C.) to a solution containing 130 mg (0.14 mmol) of 13-O-[2-(p-nitrobenzenesulfonyloxy)ethoxy]methyl-5-O-t-butyldimethylsilyl-22,23-dihydro avermectin B1a/B1b aglycones from Example 26 in 5.0 ml of dry methylene chloride. Stirring was continued at 23° C. until the 36-hour reaction was complete as determined by HPLC and TLC. The solution was diluted with methylene chloride, extracted with aqueous sodium bicarbonate and dried over anhydrous sodium bicarbonate. Evaporation of the solvent in vacuo left 114 mg of the crude product as a foam solid. The product was chromatographically purified on silica gel using methylene chloridemethanol-water furnishing 65 mg of 13-O-[2-(morpholin-1-yl)ethoxy]-methyl-5-O-t-butyldimethylsilyl-22,23-dihydro avermectin B1a/B1b aglycones, 96% purity by HPLC. The structure was confirmed by nuclear magnetic resonance and mass spectrometry.

EXAMPLE 33

The procedure of Example 3 is followed thereby obtaining the corresponding 13-O-substituted alkoxymethyl, 13-O-polyalkoxy methyl and 13-O-alkoxymethyl-22,23-dihydro avermectin B1a/B1b aglycones as shown in Tables IVa, b, and c, respectively, below:

TABLE IVa

13-O—Alkoxymethyl-22,23-dihydro avermectin B1a/B1b aglycones by deblocking of the corresponding 5-O—t-butyldimethylsilyl derivatives following the procedure of Example 3.

| 13-Substituent | $E^{1\%}_{1cm}$ at $\lambda^{MeOH}_{max}$ 244 nm | % Purity by HPLC | Identification[1] |
|---|---|---|---|
| 13-O—(2-Methoxyethoxy)methyl | 450 | 96 | A, B, C, D, E, F |
| 13-O—Isobutoxymethyl | 461 | 96 | A, B, C, D, E, F |
| 13-O—[2-(2-Methoxyethoxy)ethoxy]methyl | 461 | 97 | A, B, C, D, E, F |
| 13-Epi-O—(2-Methoxyethoxy)methyl | 466 | 93 | A, B, C, D, E, F |
| 13-Epi-O—Benzyloxy- | 343 | 95 | A, B, D, E, |

TABLE IVa-continued

13-O—Alkoxymethyl-22,23-dihydro avermectin B1a/B1b aglycones by deblocking of the corresponding 5-O—t-butyldimethylsilyl derivatives following the procedure of Example 3.

| 13-Substituent | $E_{1\,cm}^{1\%}$ at $\lambda_{max}^{MeOH}$ 244 nm | % Purity by HPLC | Identification[1] |
|---|---|---|---|
| methyl | | | F |
| 13-O—Benzyloxymethyl | 430 | 96 | A, B, C, D, E, F |

[1] See footnote 2 of Table II.

TABLE IVb

13-O—Polyalkoxy methyl-22,23-dihydro avermectin B1a/B1b aglycones by deblocking of the corresponding-5-O—t-butyldimethylsilyl derivatives following the procedure of Example 3.

| 13-O—Substituent | $E_{1\,cm}^{1\%}$ at $\lambda_{max}^{MeOH}$ 244 nm | % Purity by HPLC | Identification[1] |
|---|---|---|---|
| 13-O—[2-(Methoxymethoxy)ethoxy]methyl | 436 | 94 | A, B, C, D, E, F |
| 13-O—[2-(2-Methoxyethoxy)methoxyethoxy]methyl | 455 | 94 | A, B, C, D, E, F |
| 13-O—(2-[2-(2-Methoxyethoxy)-ethoxy]methoxyethoxy)methyl | 455 | 91 | A, B, C, D, E, F |
| 13-O—[2-(Benzyloxymethoxy)ethoxy]methyl | 358 | 96 | A, B, D, E, F |

[1] See footnote 2 of Table II.

TABLE IVc

13-O—Substituted alkoxymethyl-22,23-dihydro avermectin B1a/B1b aglycones by deblocking of the corresponding 5-O—t-butyldimethylsilyl derivatives following the procedure of Example 3.

| 13-O—Substituent | $E_{1\,cm}^{1\%}$ at $\lambda_{max}^{MeOH}$ 244 nm | % Purity by HPLC | Identification[1] |
|---|---|---|---|
| (2-Acetoxyethoxy)methyl | 366 | 94 | A, B, C, D, E, F |
| (2-Hydroxyethoxy)methyl | 462 | 100 | A, B, C, D, E, F |
| (2-Chloroethoxy)methyl | 405 | 94 | A, B, D, E, F, G |
| (2-Dimethylaminoethoxy)methyl | 463 | 91 | A, B, C, D, E, F, G |
| [2-(Morpholin-1-yl)ethoxy]methyl | 411 | 96 | A, B, C, D, E, F |

[1] See footnote 2, Table II.

EXAMPLE 34

13-(2-Methoxyethoxy)methoxy-5-O-t-butyldimethylsilyl milbemycin $\alpha_1$

Following the procedure of Example 16, 60 mg of 13-hydroxy-5-O-t-butlydimethylsilyl milbemycin $\alpha_1$ [the 13-hydroxy milbemycin $\alpha_1$ obtained according to the procedure described in U.S. Pat. No. 4,134,973 and the 5-OH protected with t-butyldimethylsilyl as described by Mrozik et al. in Tetrahedron Letters 24, pp. 5333–5336 (1983)] is treated with 117 μl of (2-methoxyethoxy)methyl chloride in a solution containing 195 μl of N,N-diisopropylethylamine and 240 μl of dry methylene chloride. 13-(2-Methoxyethoxy)methoxy-5-O-t-butyldimethylsilyl milbemycin $\alpha_1$ is obtained.

EXAMPLE 35

13-(2-Methoxyethoxy)methoxy milbemycin $\alpha_1$

Following the procedure of Example 3, 80 mg of 13-(2-methoxyethoxy)methoxy-5-O-t-butyldimethylsilyl milbemycin $\alpha_1$ is reacted in a solution containing 0.5% para-toluenesulfonic acid monohydrate in 5.0 ml of methanol furnishing 13-(2-methoxyethoxy)methoxy milbemycin $\alpha_1$.

EXAMPLE 36

13-(2-Acetoxyethoxy)methoxy-5-O-t-butyldimethylsilyl milbemycin $\alpha_3$

Following the procedure of Example 18, 2.8 g of 13-hydroxy-5-O-t-butyldimethylsilyl milbemycin $\alpha_3$ [the 13-hydroxy milbemycin $\alpha_3$ is obtained according to the procedure described in U.S. Pat. No. 4,134,973 and the 5-OH is protected with t-butyldimethylsilyl as described by Mrozik et al. in Tetrahedron Letters 24, pp. 5333–5336 (1983)] is treated with 9.0 ml of (2-acetoxyethoxy)methyl bromide in a solution containing 5.5 ml of N,N-diisopropylethylamine in 11 ml of methylene chloride furnishing 13-(2-acetoxyethoxy)methoxy-5-O-t-butyldimethylsilyl milbemycin $\alpha_3$.

EXAMPLE 37

13-(2-Hydroxyethoxy)methoxy-5-O-t-butyldimethylsilyl milbemycin $\alpha_3$

Following the procedure of Example 19, 1.70 g of 13-(2-acetoxyethoxy)methoxy-5-O-t-butyldimethylsilyl milbemycin $\alpha_3$ is reacted in 50 ml of cold (0° to 5° C.) saturated methanolic ammonia providing 13-(2-hydroxyethoxy)methoxy-5-O-t-butyldimethylsilyl milbemycin $\alpha_3$.

EXAMPLE 38

13-[2-(Methoxymethoxy)ethoxy]methoxy-5-O-t-butyldimethylsilyl milbemycin $\alpha_3$ Following the procedure of Example 20, 90 mg of 13-(2-hydroxyethoxy)methoxy-5-O-t-butyldimethylsilyl milbemycin $\alpha_3$ is reacted with 100 μl of chloromethyl methyl ether in a solution containin 271 μl of N,N-diisopropylethylamine and 0.36 ml of methylene chloride furnishing 13-[2-(methoxymethoxy)ethoxy]-methoxy-5-O-t-butyldimethylsilyl milbemycin $\alpha_3$.

EXAMPLE 39

13-[2-(Methoxymethoxy)ethoxy]methoxy milbemycin $\alpha_3$

Following the procedure of Example 3, 80 mg of 13-(2-methoxymethoxyethoxy)methoxy-5-O-t-butyl-dimethylsilyl milbemycin $\alpha_3$ is deblocked in 5.0 ml of methanolic 0.5% para-toluenesulfonic acid monohydrate providing 13-[2-(methoxymethoxy)ethoxy]methoxy milbemycin $\alpha_3$.

What is claimed is:

1. A compound having the formula:

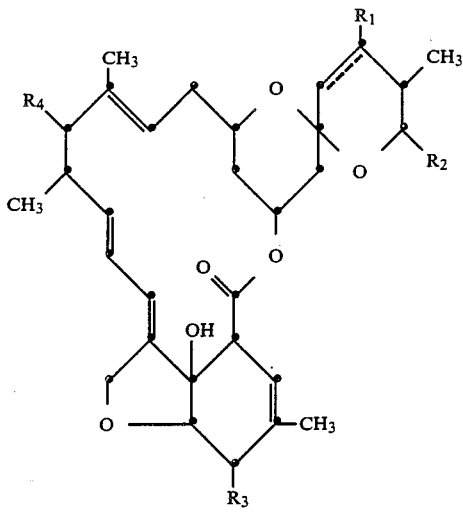

wherein the broken line indicates a single or a double bond; wherein $R_1$ is H, —OH, provided that the broken line indicates a single bond when $R_1$ is OH;

$R_2$ is methyl, ethyl, iso-propyl or sec-butyl;

$R_3$ is OH, $OCH_3$, $OSi(CH_3)_2C(CH_3)_3$;

$R_4$ is X—$(CH_2)_n$—O—$CH_2$O— wherein n is an integer ranging from 1–6 and X is hydrogen; alkyl $C_{1-6}$; alkoxy $C_{1-6}$; polyalkoxy, H—$[(CH_2)_pO]_m$— wherein m is an integer from 2–6 and p is an integer ranging from 1–6; phenyl, phenyl (alkoxy $C_{1-4}$), acyloxy $C_{1-4}$; hydroxy; phenyl poly(alkoxy), —$[(CH_2)_pO]_m$— wherein m and p are as defined above; halogen; amino; alkylamino $C_{1-5}$; dialkylamino $C_{2-8}$; or heterocyclic 3–6 membered nitrogen containing ring optionally containing an additional oxygen, sulfur or nitrogen heteroatom wherein the ring nitrogen is bonded to the alkoxy group.

2. The compound of claim 1 wherein n is 1–3; X is selected from the group consisting of hydrogen, alkoxy $C_{1-4}$, polyalkoxy H—$[(CH_2)_pO]_m$— wherein p and m are 1–3, phenyl, phenylalkoxy $C_{1-4}$, acyloxy $C_{1-4}$, halogen, amino, alkylamino $C_{1-3}$, dialkylamino $C_{2-6}$, aziridino, pyrrolidino, morpholino, thiomorpholino and 4-methylpiperazino.

3. The compound of claim 2 where n is 2 and X is methoxy.

4. The compound of claim 3 which is
13-O-(2-methoxyethoxy)methyl-22,23-dihydro avermectin B1a/B1b aglycone;
13-O-(2-methoxyethoxy)methyl avermectin B1a/B1b aglycone;
13 -O-(2-methoxyethoxy)methyl avermectin B2a/B2b aglycone;
13-(2-methoxyethoxy)methyl milbemycin $\alpha_1$; or
13-(2-methoxyethoxy)methoxy milbemycin $\alpha_3$.

5. The compound of claim 2 which is
13-O-[2-(2-methoxyethoxy)ethoxy]methyl-22,23-dihydro avermectin B1a/B1b aglycone;
13-O-[2-(2-methoxyethoxy)methoxyethoxy]methyl-22,23-dihydro avermectin B1a/B1b aglycone;
13-O-[2-(methoxymethoxy)ethoxy]methyl-22,23-dihydro avermectin B1a/B1b aglycone;
13-[2-(methoxymethoxy)ethoxy]methoxy milbemycin $\alpha_1$; or
13-[2-(methoxymethoxy)ethoxy]methoxy milbemycin $\alpha_3$.

6. The compound of claim 2 which is 13-O-benzyloxymethyl-22,23-dihydro avermectin B1a/B1b aglycone.

7. The compound of claim 2 which is 13-O-methoxymethyl-22,23-dihydro avermectin B1a/B1b aglycone.

8. The compound of claim 2 which is 13-O-(2-chloroethoxy)methyl-22,23-dihydro avermectin B1a/B1b aglycone.

9. The compound of claim 2 which is 13-O-[2-(dimethylaminoethoxy)methyl-22,23-dihydro avermectin B1a/B1b aglycone.

10. The compound of claim 2 which is 13O-[2-(morpholin-1-yl)ethoxy]methyl-22,23-dihydro avermectin B1a/B1b aglycone.

11. A pharmaceutical composition for treatment of animals infected with parasites which comprises a therapeutically effective dosage amount of a compound of claim 1 and a pharmaceutically acceptable carrier.

12. A method treating an animal suffering from a parasitic condition which comprises administering a therapeutically effective amount of a compound of claim 1.

* * * * *